(12) United States Patent
Drochner et al.

(10) Patent No.: US 10,869,682 B2
(45) Date of Patent: Dec. 22, 2020

(54) CUTTING MECHANISMS FOR SURGICAL END EFFECTOR ASSEMBLIES, INSTRUMENTS, AND SYSTEMS

(71) Applicant: COVIDIEN LP, Mansfield, MA (US)

(72) Inventors: Thomas E. Drochner, Longmont, CO (US); James D. Allen, IV, Broomfield, CO (US); Gary M. Couture, Ward, CO (US); William H. Nau, Jr., Longmont, CO (US); Robert M. Sharp, Boulder, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 759 days.

(21) Appl. No.: 15/205,067

(22) Filed: Jul. 8, 2016

(65) Prior Publication Data
US 2018/0008298 A1 Jan. 11, 2018

(51) Int. Cl.
*A61B 17/285* (2006.01)
*A61B 17/28* (2006.01)
(Continued)

(52) U.S. Cl.
CPC ...... *A61B 17/285* (2013.01); *A61B 17/00234* (2013.01); *A61B 17/28* (2013.01);
(Continued)

(58) Field of Classification Search
CPC . A61B 17/00234; A61B 17/28; A61B 17/285; A61B 2018/1452; A61B 2034/306
See application file for complete search history.

(56) References Cited

U.S. PATENT DOCUMENTS 5,797,941 A 8/1998 Schulze et al.
6,312,435 B1 * 11/2001 Wallace ................. A61B 34/70
606/130

(Continued)

FOREIGN PATENT DOCUMENTS

WO 2016/025132 A1 2/2016

OTHER PUBLICATIONS

Partial European search report issued in corresponding EP application No. 17180236.6 dated Dec. 1, 2017.

*Primary Examiner* — Thomas A Giuliani
*Assistant Examiner* — Christine A Dedoulis
(74) *Attorney, Agent, or Firm* — Carter, DeLuca & Farrell LLP

(57) ABSTRACT

A surgical system includes an attaching device having an end effector disposed at the distal end thereof. The end effector includes a support member, a wrist pivot pivotably coupling the end effector to the attaching device, and first and second jaw members pivotably coupled to one another and the support member. A first cable is operably coupled to the wrist pivot and configured to articulate the end effector relative to the attaching device. Second and third cables are operably coupled to the jaw members and configured to pivot the jaw members relative to the support member. A first actuation of the second and third cables collectively pivots the first and second jaw members relative to the support member. A second actuation of the second and third cables pivots the first and second jaw members relative to one another and the support member between a spaced-apart position and an approximated position.

6 Claims, 8 Drawing Sheets

(51) Int. Cl.
    *A61B 18/14*     (2006.01)
    *A61B 34/00*     (2016.01)
    *A61B 34/30*     (2016.01)
    *A61B 17/00*     (2006.01)
    *A61B 17/29*     (2006.01)

(52) U.S. Cl.
CPC ...... *A61B 18/1442* (2013.01); *A61B 18/1445* (2013.01); *A61B 34/30* (2016.02); *A61B 34/71* (2016.02); *A61B 2017/00314* (2013.01); *A61B 2017/00323* (2013.01); *A61B 2017/2927* (2013.01); *A61B 2017/2938* (2013.01); *A61B 2018/1452* (2013.01); *A61B 2018/1455* (2013.01); *A61B 2034/306* (2016.02)

(56) References Cited

U.S. PATENT DOCUMENTS

| | | |
|---|---|---|
| 6,652,521 B2 | 11/2003 | Schulze |
| 7,540,872 B2 | 6/2009 | Schechter et al. |
| 7,955,332 B2 | 6/2011 | Arts et al. |
| 8,123,743 B2 * | 2/2012 | Arts .................. A61B 17/2812 606/39 |
| 8,241,282 B2 | 8/2012 | Unger et al. |
| 8,287,536 B2 | 10/2012 | Mueller et al. |
| 8,425,511 B2 | 4/2013 | Olson |
| 8,551,129 B2 * | 10/2013 | Lary ............... A61B 17/320016 606/159 |
| 8,591,510 B2 | 11/2013 | Allen, IV et al. |
| 8,628,557 B2 | 1/2014 | Collings et al. |
| 8,647,343 B2 | 2/2014 | Chojin et al. |
| 8,652,135 B2 | 2/2014 | Nau, Jr. |
| 8,858,547 B2 | 10/2014 | Brogna |
| 8,888,775 B2 | 11/2014 | Nau, Jr. et al. |
| 8,961,514 B2 | 2/2015 | Garrison |
| 9,039,732 B2 | 5/2015 | Sims et al. |
| 9,055,961 B2 | 6/2015 | Manzo et al. |
| 2002/0099368 A1 * | 7/2002 | Schulze ............ A61B 18/1445 606/45 |
| 2009/0062792 A1 * | 3/2009 | Vakharia ........... A61B 18/1492 606/45 |
| 2012/0095460 A1 * | 4/2012 | Rooks .................. A61B 17/28 606/45 |
| 2013/0123837 A1 | 5/2013 | Roy et al. |
| 2015/0066022 A1 | 3/2015 | Shelton, IV et al. |
| 2015/0127045 A1 * | 5/2015 | Prestel .................. A61B 17/29 606/208 |
| 2016/0058441 A1 * | 3/2016 | Morgan .............. A61B 17/0644 606/219 |
| 2018/0036025 A1 * | 2/2018 | Drochner ............ A61B 17/295 |
| 2018/0161112 A1 * | 6/2018 | Weir .................. A61B 18/1445 |

\* cited by examiner

CUTTING MECHANISMS FOR SURGICAL END EFFECTOR ASSEMBLIES, INSTRUMENTS, AND SYSTEMS

BACKGROUND

Technical Field

The present disclosure relates to surgical devices and, more particularly, to cutting mechanisms for use with surgical end effector assemblies, instruments, and systems.

Background of Related Art

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

In accordance with aspects of the present disclosure, a surgical system is provided including first, second, and third cables, an attaching device defining a distal end, an end effector assembly disposed at the distal end of the attaching device. The end effector assembly includes a support member defining a proximal end and a distal end, a wrist pivot disposed proximate the proximal end of the support member, and first and second jaw members. The wrist pivot pivotably couples the end effector assembly to the attaching device. The first and second jaw members are disposed at the distal end of the support member and are pivotably coupled to one another and the support member. The first cable is operably coupled to the wrist pivot and configured to articulate the end effector assembly relative to the attaching device in first and second directions. The second and third cables are operably coupled to the first and second jaw members, respectively, and configured to pivot the first and second jaw members, respectively, relative to the support member in third and fourth directions perpendicular to the first and second directions. A first actuation of the second and third cables collectively pivots the first and second jaw members relative to the support member while maintaining the first and second jaw members in fixed position relative to one another. A second actuation of the second and third cables pivots the first and second jaw members relative to one another and the support member between a spaced-apart position and an approximated position.

In an aspect of the present disclosure, the first actuation of the second and third cables includes actuating the second and third cables in a similar manner and the second actuation of the second and third cables includes actuating the second and third cables in an opposite manner.

In another aspect of the present disclosure, the first actuation of the second and third cables includes actuating the second and third cables in an opposite manner, and the second actuation of the second and third cables includes actuating the second and third cables in a similar manner.

In yet another aspect of the present disclosure, the system further includes first, second, and third motors operably coupled to the first, second, and third cables, respectively, and configured to selectively actuate the respective first, second, and third cables.

In still another aspect of the present disclosure, the end effector assembly further comprises a cutting mechanism including at least one knife configured to advance at least partially between the first and second jaw members. In such aspects, a fourth cable may be operably coupled to the cutting mechanism and configured to selectively advance the at least one knife. Additionally, a fourth motor may be operably coupled to the fourth cable and configured to selectively actuate the fourth cable.

In still yet another aspect of the present disclosure, the system further includes a robot arm having the attaching device disposed proximate a free end thereof.

An end effector assembly provided in accordance with aspects of the present disclosure and configured for use with a surgical instrument or surgical system includes first and second jaw members each including an outer jaw housing and a tissue-treating plate. The second jaw member and, in some aspects, also the first jaw member, defines a longitudinally-extending channel therethrough. One or both of the first or second jaw members is pivotable relative to the other between a spaced-apart position and an approximated position. The end effector assembly further includes a cutting mechanism disposed within the second jaw member. The cutting mechanism includes an actuation shaft slidably disposed within the second jaw member and a plurality of knives. Each knife is pivotably coupled to the actuation shaft and the second jaw member at offset positions such that sliding of the actuation shaft through the second jaw member pivots the plurality of knives between a retracted position, wherein the plurality of knives is fully disposed within the longitudinally-extending channel of the second jaw member, and an extended position, wherein the plurality of knives extends between the first and second jaw members.

In an aspect of the present disclosure, each knife of the plurality of knives is movable in a sweeping pattern between the first and second jaw members.

In another aspect of the present disclosure, the sweeping patterns of adjacent knifes of the plurality of knifes overlap one another.

In still another aspect of the present disclosure, a lead screw is disposed within the second jaw member and a proximal connector is associated with the actuation shaft. The lead screw and proximal connector are disposed in meshed engagement with one another such that rotation of the lead screw translates the proximal connector to thereby slide the actuation shaft through the second jaw member.

Another end effector assembly configured for use with a surgical instrument or surgical system and provided in accordance with aspects of the present disclosure includes first and second jaw members and a cutting mechanism. Each jaw member includes an outer jaw housing and a tissue-treating plate. The second jaw member and, in some aspects, also the first jaw member, defines a longitudinally-extending channel therethrough. Either or both of the first and second jaw members is pivotable relative to the other between a spaced-apart position and an approximated position. The cutting mechanism is disposed within the second jaw member and includes a knife and a pull-wire. The knife is disposed at least partially within the longitudinally-extending channel of the second jaw member and defines a cutting surface. The knife is pivotable relative to the second jaw member from a storage position, wherein the knife is fully disposed within the longitudinally-extending channel of the second jaw member and the cutting surface is oriented towards the first jaw member, and a use position, wherein the knife extends between the first and second jaw members and the cutting surface is oriented in a proximally-facing direction. The pull-wire extends through the second jaw member and is coupled to the knife proximate a distal end of the pull-wire. The pull-wire is configured for proximal pulling relative to the second jaw member to initially pivot the knife from the storage position to the use position and to subsequently translate the knife through the longitudinally-extending channel of the second jaw member in a distal-to-proximal direction led by the cutting surface thereof.

In an aspect of the present disclosure, a biasing member is operably coupled between the knife and the second jaw member. The biasing member is configured to initially bias the knife distally relative to the longitudinally-extending channel of the second jaw member and to subsequently bias the knife towards the storage position.

In another aspect of the present disclosure, at least one guide track is defined within the second jaw member and configured to guide translation of the knife through the longitudinally-extending channel.

In still another aspect of the present disclosure, the knife is pivotably coupled to the second jaw member via a pivot pin. In such aspects, the pivot pin is disposed within the guide track and configured to guide translation of the knife through the longitudinally-extending channel.

Another end effector assembly configured for use with a surgical instrument or surgical system and provided in accordance with aspects of the present disclosure includes first and second jaw members and a cutting mechanism. The first and second jaw members each include an outer jaw housing and a tissue-treating plate. The second jaw member and, in some aspects, also the first jaw member, defines a longitudinally-extending channel therethrough. The first and/or second jaw member is pivotable relative to the other between a spaced-apart position and an approximated position. The cutting mechanism is disposed within the second jaw member and includes an actuation shaft slidably disposed within the second jaw member, a support base disposed within the longitudinally-extending channel of the second jaw member and configured to move at least partially towards and away from the first jaw member, a knife defining a longitudinally-extending cutting edge mounted on the support base, and a plurality of linkages operably coupled between the actuation shaft and the support base such that longitudinally sliding the actuation shaft through the second jaw member moves the support base to thereby move the knife between a retracted position, wherein the knife is fully disposed within the longitudinally-extending channel of the second jaw member, and an extended position, wherein the knife extends between the first and second jaw members.

In an aspect of the present disclosure, at least one guide bracket is disposed within the second jaw member. The at least one guide bracket is configured to receive at least a portion of the support base to confine the support base to movement towards and away from the first jaw member.

In another aspect of the present disclosure, the support base includes at least one leg configured for slidable receipt within the at least one guide bracket.

In yet another aspect of the present disclosure, the knife is configured to move in a sweeping pattern between the first and second jaw members.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1A:
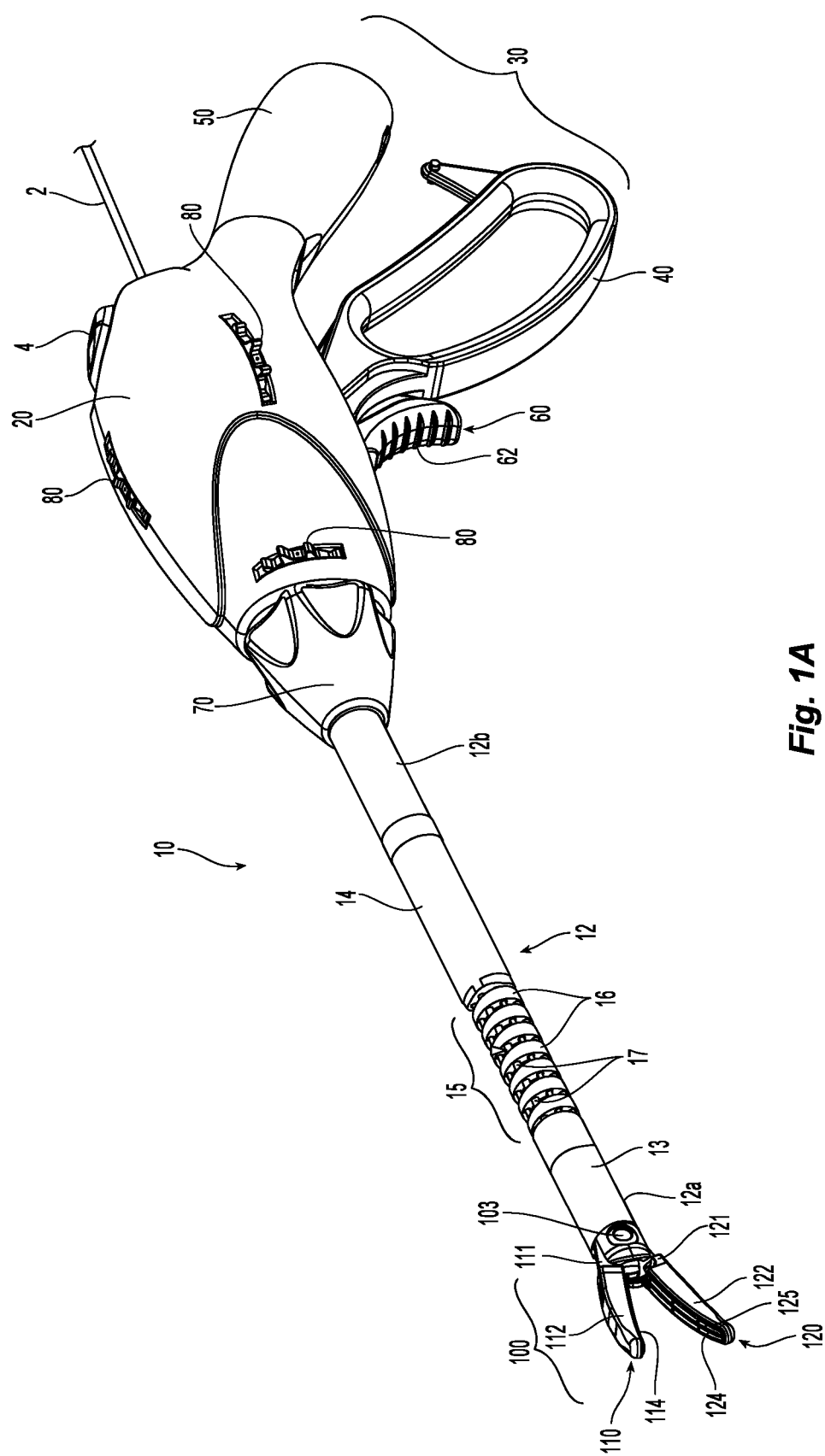
FIG. 1A is a perspective view of endoscopic surgical forceps exemplifying the aspects and features of the present disclosure, wherein the shaft of the endoscopic surgical forceps is disposed in a non-articulated position and wherein the jaw members of the endoscopic surgical forceps are disposed in a spaced-apart position.
Figure 1B:
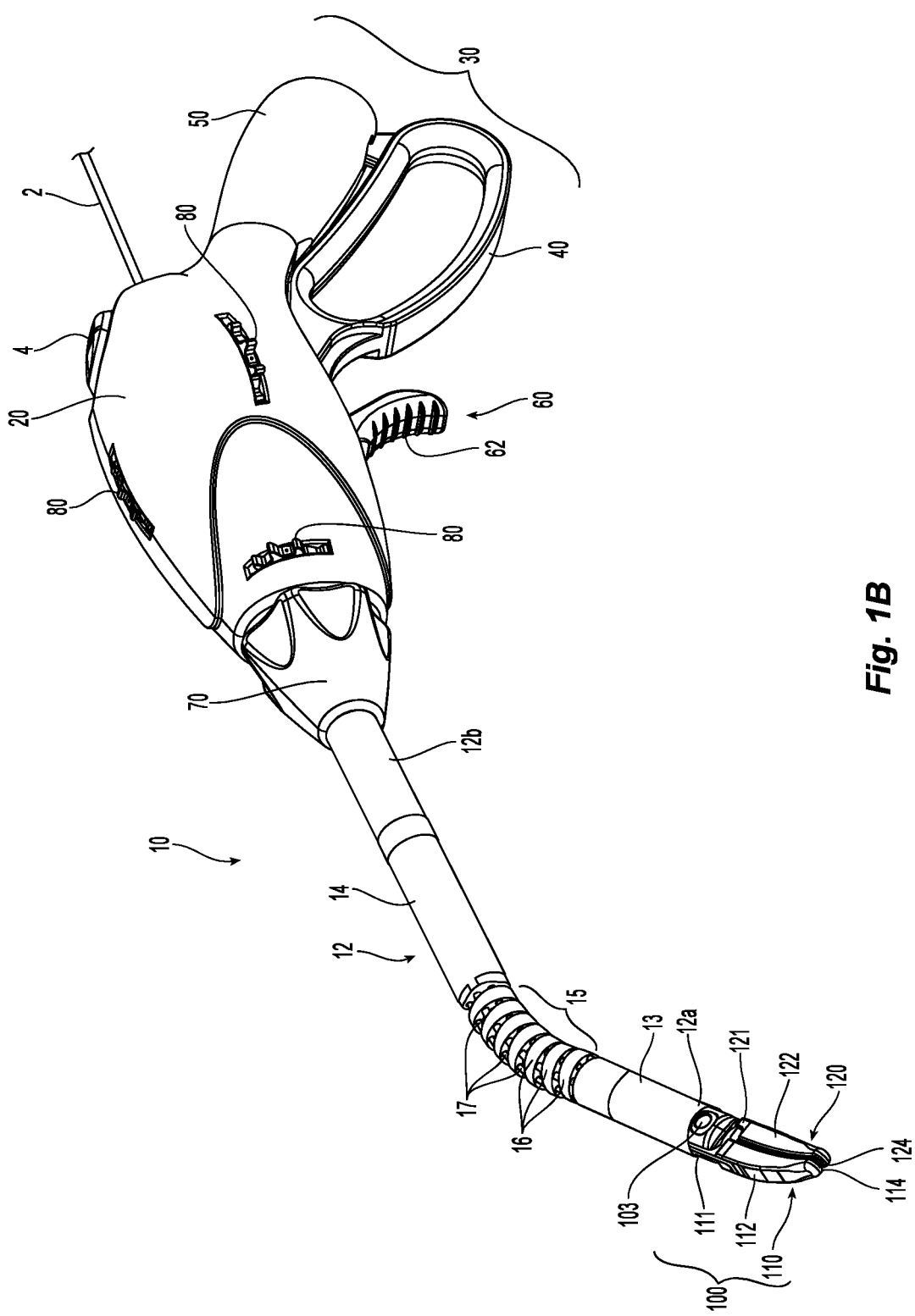
FIG. 1B is a perspective view of the endoscopic surgical forceps of FIG. 1A, wherein the shaft of the endoscopic surgical forceps is disposed in an articulated position and wherein the jaw members of the endoscopic surgical forceps are disposed in an approximated position.

Referring generally to FIGS. 1A and 1B, an endoscopic surgical forceps exemplifying the aspects and features of the present disclosure is shown generally identified by reference numeral 10. For the purposes herein, endoscopic surgical forceps 10 is generally described. Aspects and features of endoscopic surgical forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a plurality of articulation actuators 80, an activation switch 4, and an end effector assembly 100. Forceps 10 further includes a shaft 12 having a distal end 12a configured to mechanically engage end effector assembly 100 and a proximal end 12b that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 of jaw members 110, 120, respectively, of end effector assembly 100. Activation switch 4 is coupled to tissue-treating plates 114, 124 and the source of energy for selectively activating the supply of energy to jaw members 110, 120 for treating, e.g., cauterizing, coagulating/desiccating, and/or sealing, tissue.

Shaft 12 of forceps 10 defines a distal segment 13 positioned towards distal end 12a thereof, a proximal segment 14 positioned towards proximal end 12b thereof, and an articulating section 15 disposed between the distal and proximal segments 13, 14, respectively. Articulating section 15 includes a plurality of articulating links 16 having a plurality of articulation cables 17 extending therethrough. Each cable 17 is operably engaged at its distal end to distal segment 13 and at its proximal end to one of the articulation actuators 80 to enable articulation of distal segment 13 and, thus, end effector assembly 100, relative to proximal segment 14 upon actuation of one or more of articulation actuators 80. In some embodiments, articulating section 15 and articulation actuators 80 are omitted, such that shaft 12 of forceps 10 does not articulate. In either configuration, rotating assembly 70 operably couples shaft 12 to housing 20 to enable selective rotation of shaft 12 and, thus, end effector assembly 100, relative to housing 20.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position (FIG. 1A) and an approximated position (FIG. 1B) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 1B).

Trigger assembly 60 includes a trigger 62 coupled to housing 20 and movable relative thereto between an unactuated position and an actuated position. Trigger 62 is operably coupled to a cutting mechanism, various embodiments of which are detailed below, to actuate the cutting mechanism to cut tissue grasped between jaw members 110, 120 of end effector assembly 100 upon actuation of trigger 62. As an alternative to a pivoting trigger 62, a slide trigger, push-button, toggle switch, or other suitable actuator may be provided.

End effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 and the source of energy (not shown), e.g., via the wires (not shown) extending from cable 2 through forceps 10, such that energy may be selectively supplied to tissue-treating plate 114 and/or tissue-treating plate 124 and conducted therebetween and through tissue disposed between jaw members 110, 120 to treat tissue. One or both of jaw members 110, 120 may further define a longitudinally-extending channel 125 (only the channel of jaw member 120 is shown).

Figure 2:
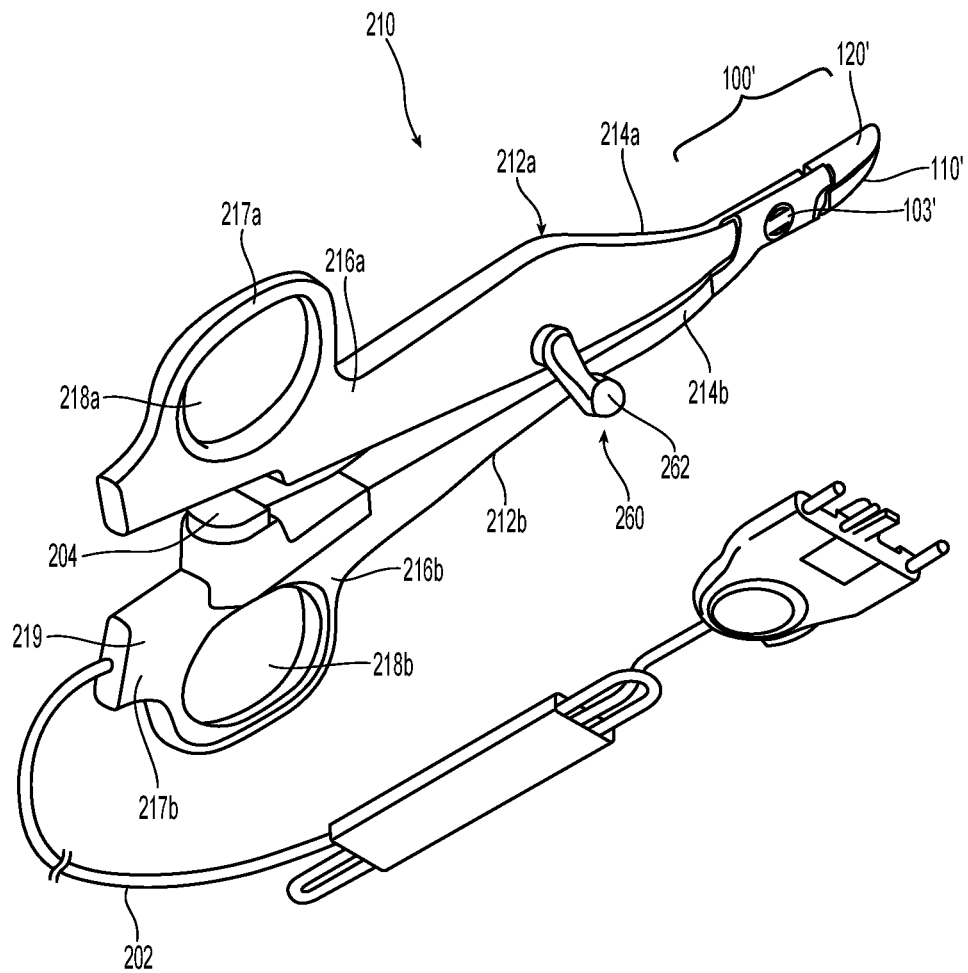
FIG. 2 is a perspective view of an open surgical forceps exemplifying the aspects and features of the present disclosure.

Referring to FIG. 2, an open surgical forceps exemplifying the aspects and features of the present disclosure is shown generally identified by reference numeral 210. For the purposes herein, open surgical forceps 210 is generally described. Aspects and features of open surgical forceps 210 not germane to the understanding of the present disclosure are omitted to avoid obscuring the aspects and features of the present disclosure in unnecessary detail.

Forceps 210 includes two elongated shaft members 212a, 212b, each having a proximal end 216a, 216b, and a distal end 214a, 214b, respectively. Forceps 210 is configured for use with an end effector assembly 100' similar to end effector assembly 100 (FIGS. 1A and 1B). More specifically, end effector assembly 100' includes first and second jaw members 110', 120' attached to respective distal ends 214a, 214b of shaft members 212a, 212b. Jaw members 110', 120' are pivotably connected about a pivot 103'. Each shaft member 212a, 212b includes a handle 217a, 217b disposed at the proximal end 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 10', e.g., shaft member 212b, includes a proximal shaft connector 219 configured to connect forceps 210 to a source of energy (not shown), e.g., a generator. Proximal shaft connector 219 secures a cable 202 to forceps 210 such that the user may selectively supply energy to jaw members 110', 120' for treating tissue and for energy-based tissue cutting. More specifically, an activation switch 204 is provided for supplying energy to jaw members 110', 120' to treat tissue upon sufficient approximation of shaft members 212a, 212b, e.g., upon activation of activation switch 204 via shaft member 212a.

Forceps 210 further includes a trigger assembly 260 including a trigger 262 coupled to one of the shaft members, e.g., shaft member 212a, and movable relative thereto between an un-actuated position and an actuated position. Trigger 262 is operably coupled to a cutting mechanism, various embodiments of which are detailed below, so as to actuate the cutting mechanism to cut tissue grasped between jaw members 110,' 120' of end effector assembly 100' upon movement of trigger 262 to the actuated position. Similarly as noted above, other suitable actuators for the cutting mechanism are also contemplated.

Figure 3A:
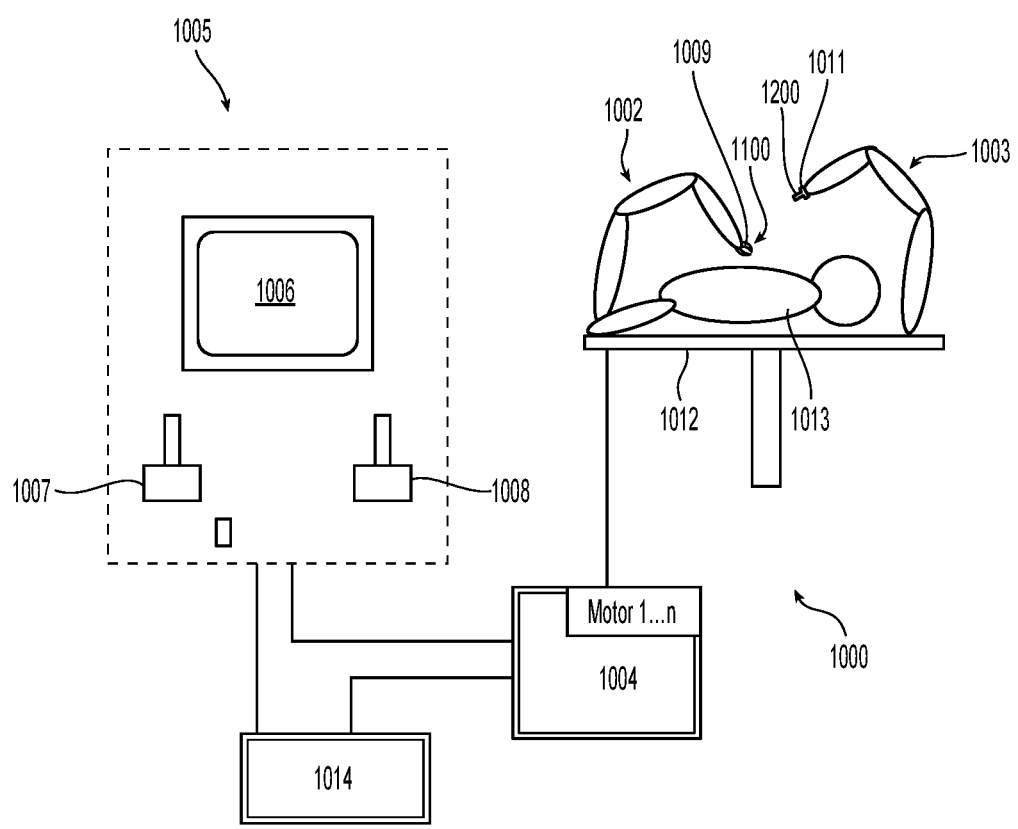
FIG. 3A is a schematic illustration of a robotic surgical system exemplifying the aspects and features of the present disclosure.

Referring generally to FIG. 3A, a robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is described in greater detail below and may be similar to end effector assemblies 100, 100' (FIGS. 1A-1B and 2, respectively), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 3B:
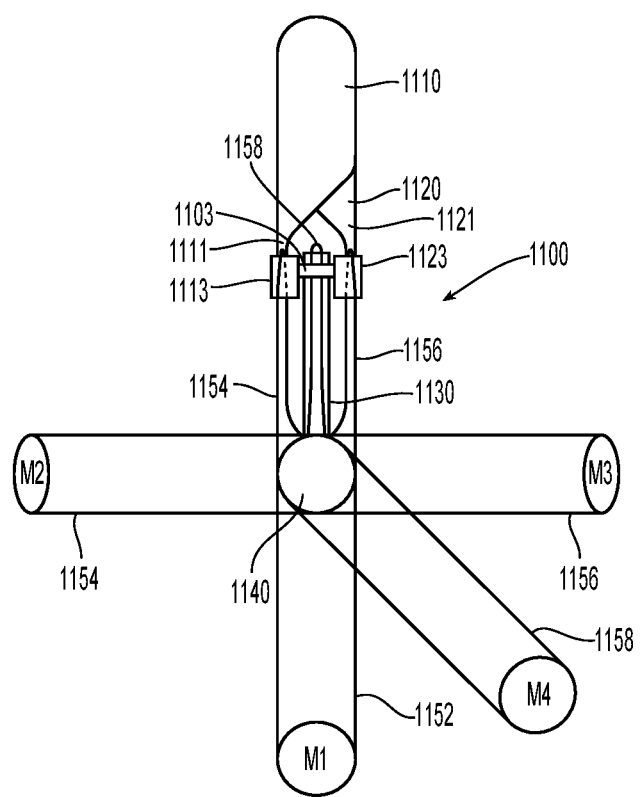
FIG. 3B is a schematic illustration of an end effector assembly configured for use with the robotic surgical system of FIG. 3A.

With additional reference to FIG. 3B, end effector assembly 1100 of robotic surgical system 1000 in schematically shown configured for use with four (4) motors M1, M2, M3, and M4 of robotic surgical system 1000, although greater or fewer motors are also contemplated. End effector assembly 1100 includes first and second jaw members 1110, 1120, respectively, a support member 1130 having a distal end pivotably supporting jaw members 1110, 1120 and a proximal end engaged with a wrist pivot 1140.

Jaw members 1110, 1120 are similar to and may include any of the features of jaw members 110, 120 of end effector assembly 100 (FIGS. 1A and 1B), except where specifically contradicted below. Proximal flanges 1111, 1121 of jaw members 1110, 1120 are pivotable relative to one another about a pivot pin 1103 for moving jaw members 1110, 1120 relative to one another between a spaced-apart position and an approximated position for grasping tissue therebetween. The proximal flange 1111, 1121 of each jaw member 1110, 1120 further includes a cable wheel 1113, 1123 mounted thereon, the importance of which is detailed below.

Support member 1130, as noted above, includes a distal end pivotably supporting jaw members 1110, 1120. More specifically, support member 1130 fixedly mounts pivot pin 1103 thereon at the distal end of support member 1130. As such, with jaw members 1110, 1120 pivotably engaged to one another about pivot pin 1103, jaw members 1110, 1120 are pivotably supported at the distal end of support member 1130. As detailed below, jaw members 1110, 1120 are permitted to pivot about pivot pin 1103 and relative to one another and support member 1130 in opposite directions to move jaw members 1110, 1120 between the spaced-apart and approximated positions, and, to pivot about pivot pin 1103 in same direction and relative to support member 1130 to collectively tilt jaw members 1110, 1120 relative to support member 1130 while maintaining jaw members 1110, 1120 in fixed position relative to one another.

Wrist pivot 1140, as noted above, is engaged to the proximal end of support member 1130. Wrist pivot 1140 is configured to operably couple support member 1130 and, thus, jaw members 1110, 1120, to attaching device 1009 of robot arm 1002 (FIG. 3A) to enable pivoting of end effector assembly 1100 relative to attaching device 1009. More specifically, wrist pivot 1140 is configured to pivot support member 1130 and jaw members 1110, 1120 relative to attaching device 1009 in directions perpendicular to the directions of pivoting of jaw members 1110, 1120 relative to support member 1130. For example, in one orientation, jaw members 1110, 1120 are configured to pivot vertically relative to one another and support member 1130, while support member 1130 is configured to pivot horizontally relative to attaching device 1009. Obviously, rotation of end effector assembly 1100 about a longitudinal axis thereof alters these directions of pivoting of jaw members 1110, 1120 and support member 1130.

Referring still to FIGS. 3A and 3B, motors M1-M4 of robotic surgical system 1000 are operably coupled to end effector assembly 1100 by way of respective cables 1152, 1154, 1156, 1158, thus enabling motors M1-M4 to drive wrist articulation of support member 1130 relative to attaching device 1009 of robot arm 1002 (FIG. 3A), pivoting of jaw members 1110, 1120 relative to one another between the spaced-apart and approximated positions, tilting of jaw members 1110, 1120 relative to support member 1130 between an aligned position and an angled position, and actuation of a cutting mechanism associated with end effector assembly 1100. Various embodiments of such cutting mechanisms are detailed below, although the configuration of motors M1-M4 and corresponding cables 1152, 1154, 1156, 1158, respectively, may similarly be used with any suitable cutting mechanism. Likewise, the cutting mechanisms detailed below need not be utilized with the configuration of motors M1-M4 and corresponding cables 1152, 1154, 1156, 1158. Further, although detailed below with respect to motors M1-M4, the aspects and features of end effector assembly 1100 may also be utilized with mechanical actuators (triggers, movable handles, rotation wheels, etc.) in place of one or more of motors M1-M4.

Cable 1152, more specifically, is operably coupled at its proximal end to motor M1 and at its distal end to wrist pivot 1140. As such, driving motor M1 "forward" pivots end effector assembly 1100 in a first direction relative to attaching device 1009 (FIG. 3A), while driving motor M2 in "reverse" pivots end effector assembly 1100 in a second, opposite direction relative to attaching device 1009 (FIG. 3A).

Cables 1154, 1156, more specifically, are operably coupled at their respective proximal ends to motors M2, M3 and at their respective distal ends to cable wheels 1113, 1123 of jaw members 1110, 1120, respectively. As such, driving motor M2 "forward" pivots jaw member 1110 relative to support member 1130 in a first direction and towards jaw member 1120, while driving motor M2 in "reverse" pivots jaw member 1110 relative to support member 1130 in a second, opposite direction and away from jaw member 1120. Driving motor M3 "forward" pivots jaw member 1120 relative to support member 1130 in the second, opposite direction and towards jaw member 1110, while driving motor M3 in "reverse" pivots jaw member 1120 relative to support member 1130 in the first direction and away from jaw member 1110. The above-detailed configuration enables tilting of both jaw members 1110, 1120 relative to support member 1130 and pivoting of jaw members 1110, 1120 relative to each other using only two motors M2, M3 and corresponding cables 1154, 1156, respectively. Tilting is accomplished by driving motors M2, M3 oppositely, that is, by driving one motor M2, M3 "forward" and by driving the other motor M2, M3 in "reverse." For example, driving motor M2 "forward" and motor M3 in "reverse" tilts jaw members 1110, 1120 in the first direction relative to support member 1130, while driving motor M2 in "reverse" and driving motor M3 "forward" tilts jaw members 1110, 1120 in the second, opposite direction relative to support member 1130. Pivoting of jaw members 1110, 1120 between the spaced-apart and approximated positions is accomplished by similarly driving motors M2, M3. For example, driving motors M2, M3 "forward" pivots jaw members 1110, 1120 from the spaced-apart position to the approximated position, while driving motors M2, M3 in "reverse" pivots jaw members 1110, 1120 from the approximated position to the spaced-apart position.

The above-detailed configuration may be reversed, e.g., wherein similar driving of motors M2, M3 effects tilting of jaw members 1110, 1120 relative to support member 1130 and opposite driving of motors M2, M3 effects relative pivoting between jaw members 1110, 1120. Regardless of the particular set-up utilized, the above-detailed configuration frees up the fourth motor M4 and associated cable 1158 for another purpose, e.g., to selectively actuate a cutting mechanism, as detailed below.

Cable 1158 is operably coupled at its proximal end to motor M4 and is configured to operably couple to a cutting mechanism at its distal end such that driving motor M4 "forward" actuates the cutting mechanism to cut tissue grasped between jaw members 1110, 1120 and such that driving motor M4 in "reverse" returns the cutting mechanism to its initial position. Alternatively, motor M4 may be configured for single-direction driving and, in such configurations, further driving of motor M4 after actuating the cutting mechanism returns the cutting mechanism to its initial position.

Referring generally to FIGS. 4A-6B, as can be appreciated, design challenges are presented in incorporating cutting mechanisms, particularly those including elongated cutting elements, into surgical instruments having articulating shafts, e.g., forceps 10 (FIGS. 1A and 1B), open surgical instruments, e.g., forceps 210 (FIG. 2), and/or robotic surgical systems, e.g., robotic surgical system 1000 (FIG. 3A). Accordingly, the various embodiments of cutting mechanisms detailed below with respect to FIGS. 4A-6B are configured to eliminate the need for elongated cutting elements, thus enabling use with articulating surgical instruments, open surgical instruments, robotic surgical systems, and any other suitable surgical instrument or system.

Figure 4A:
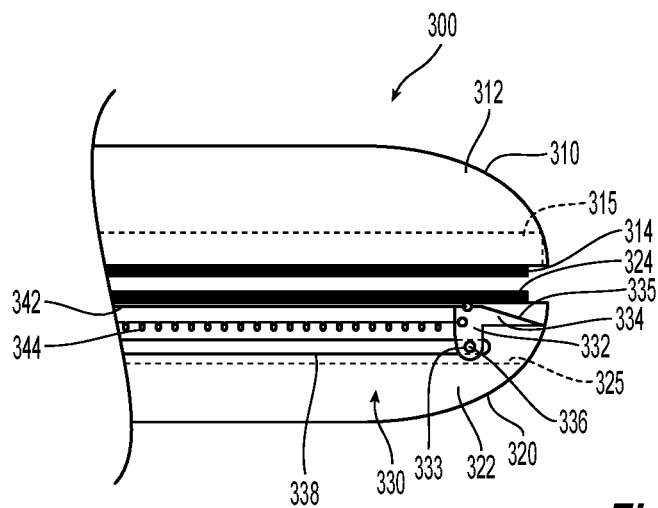
FIG. 4A is a longitudinal, cross-sectional view of an end effector assembly configured for use with the forceps of FIG. 1A, the forceps of FIG. 2, and/or the system of FIG. 3, wherein the knife thereof is disposed in a storage position.
Figure 4B:
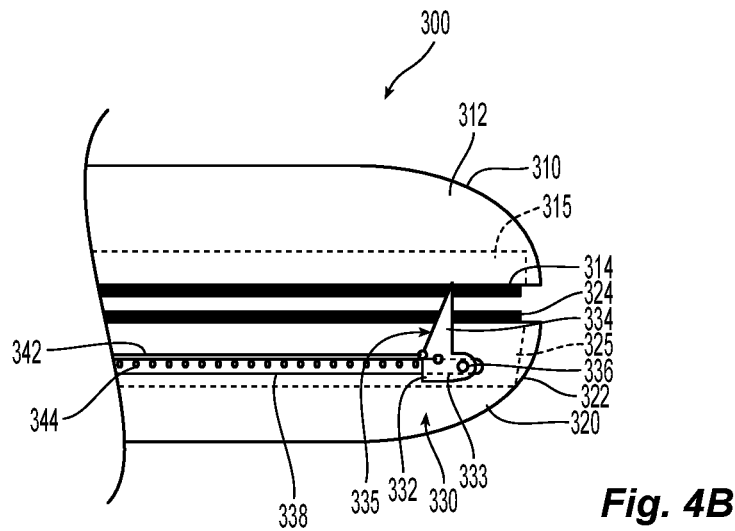
FIG. 4B is a longitudinal, cross-sectional view of the end effector assembly of FIG. 4A, wherein the knife is disposed in a use position and translating from a distal end of the end effector assembly towards a proximal end thereof.
Figure 4C:
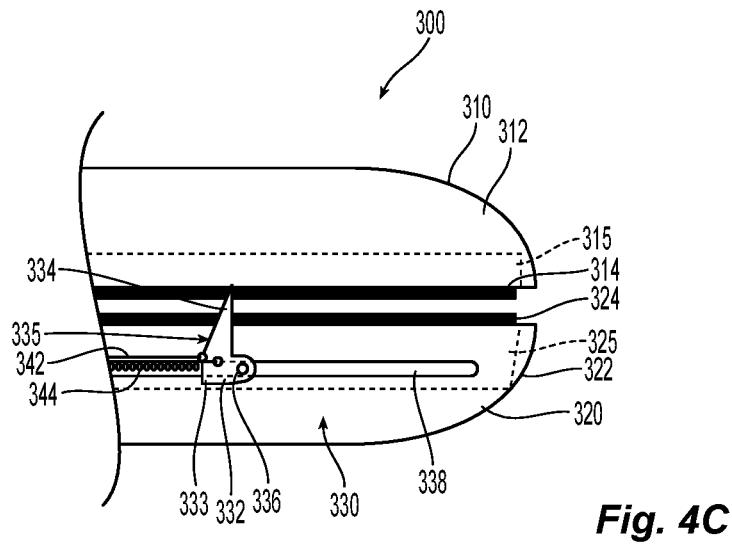
FIG. 4C is a longitudinal, cross-sectional view of the end effector assembly of FIG. 4A, wherein the knife is disposed in the use position having translated further towards the proximal end of the end effector assembly.

With reference to FIGS. 4A-4C, an end effector assembly provided in accordance with the present disclosure and configured for use with forceps 10 (FIGS. 1A-1B), forceps 210 (FIG. 2), robotic surgical system 1000 (FIG. 3A), and/or any other suitable surgical instrument or system is shown generally identified by reference numeral 300.

End effector assembly 300 is similar to end effector assemblies 100, 100', 1100 (FIGS. 1A-1B, 2, 3A, respectively) and, thus, only differences therebetween will be described in detail below for purposes of brevity. End effector assembly 300 includes first and second jaw members 310, 320 each including a jaw housing 312, 322, a tissue-treating plate 314, 324, and a longitudinally-extending channel 315, 325, although in some embodiments only one jaw member 310, 320 includes a channel 315, 325.

One of the jaw members, e.g., jaw member 320, includes a cutting mechanism 330 housed within jaw housing 322 thereof. Cutting mechanism 330 includes a knife 332, a pin 336, a pair of guide tracks 338, a pull-wire 342, and a biasing member 344. Knife 332 defines a base 333 having a cutting portion 334 extending therefrom. Cutting portion 334 defines a cutting edge 335. Knife 332 is both rotatable and translatable relative to and through jaw member 320, as detailed below. Pin 336 extends transversely through and is engaged with base 333 of knife 332 such that a portion of pin 336 extends transversely from either side of base 333 of knife 332. Guide tracks 338 are defined within the opposed longitudinally-extending walls of jaw member 320 that define channel 325 and extend longitudinally along jaw member 320. Guide tracks 338 are configured to receive the portions of pin 336 that extend transversely from either side of base 333 of knife 332 to guide translation of knife 332 through channel 325 and relative to jaw member 320, as detailed below.

Pull-wire 342 is engaged to base 333 of knife 332 at the proximal end of pull-wire 342 and extends proximally through jaw member 320. Pull-wire 342 may extend proximally from end effector assembly 300 through and/or around articulating components, pivoting components, and/or other components of the surgical instrument used with end effector assembly 300. Pull-wire 342 defines a flexible configuration so as not to interrupt articulation, pivoting, etc. of the surgical instrument used with end effector assembly 300. The actuator, e.g., trigger, of the surgical instrument used with end effector assembly 300 may be operably coupled to pull-wire 342 such that, upon actuation of the trigger, pull-wire 342 is pulled proximally. Alternatively or additionally, pull-wire 342 may be coupled to an appropriate cable and motor (or other actuator) such that, upon actuation, pull-wire 342 is pulled proximally.

Biasing member 344 extends longitudinally through channel 325 of jaw member 320 and is engaged at its distal end to base 333 of knife 332 at a position offset from pin 336 and at its proximal end (not shown) to jaw member 320. Biasing member 344 defines an elongated configuration at-rest and is biased to resist compression. As a result of this configuration of biasing member 344 and the fact that biasing member 344 is engaged to base 333 of knife 332 at a position offset from pin 336, biasing member 344 serves to bias knife 332 towards a storage position, wherein knife 332 is fully disposed within channel 325 at the distal end thereof and wherein knife 332 is oriented such that cutting edge 335 generally faces jaw member 310. The storage position of knife 332 is illustrated in FIG. 4A. Upon initial proximal pulling of pull-wire 342, knife 332 is rotated, against the bias of biasing member 344, from the storage position to a use position, wherein knife 332 is rotated 90 degrees such that knife 332 extends from channel 325 towards jaw member 310 (and, in some embodiments, at least partially into channel 315 thereof) and such that cutting edge 335 of knife 332 is oriented in a generally proximally-facing direction. The use position of knife 332 is illustrated in FIG. 4B. Upon further proximal pulling of pull-wire 342, knife 332 is pulled longitudinally through channel 325 (and, in some embodiments channel 315) in a distal to proximal direction, as illustrated in FIGS. 4B-4C, to enable knife 332, led by cutting edge 335, to cut tissue grasped between jaw members 310, 320.

Upon release of tension on pull-wire 342, biasing member 344 biases knife 332 back towards the distal, storage position (FIG. 4A). More specifically, upon release of tension on pull-wire 342, knife 332 is translated distally through channel 325 of jaw member 320 (and, in some embodiments, channel 315 of jaw member 310) to the distal end thereof and is thereafter rotated back to the storage position under the bias of biasing member 344. In some embodiments, the edge of knife 332 opposite cutting edge 335 may also define a cutting edge to enable cutting of tissue in the proximal to distal direction as knife 332 returns to the distal storage position under the bias of biasing member 344.

Figure 5A:
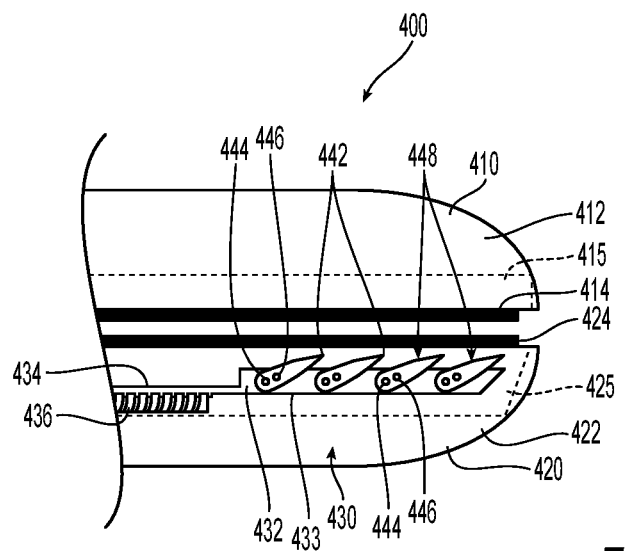
FIG. 5A is a longitudinal, cross-sectional view of another end effector assembly configured for use with the forceps of FIG. 1A, the forceps of FIG. 2, and/or the system of FIG. 3, wherein the knife chips thereof are disposed in a retracted position.
Figure 5B:
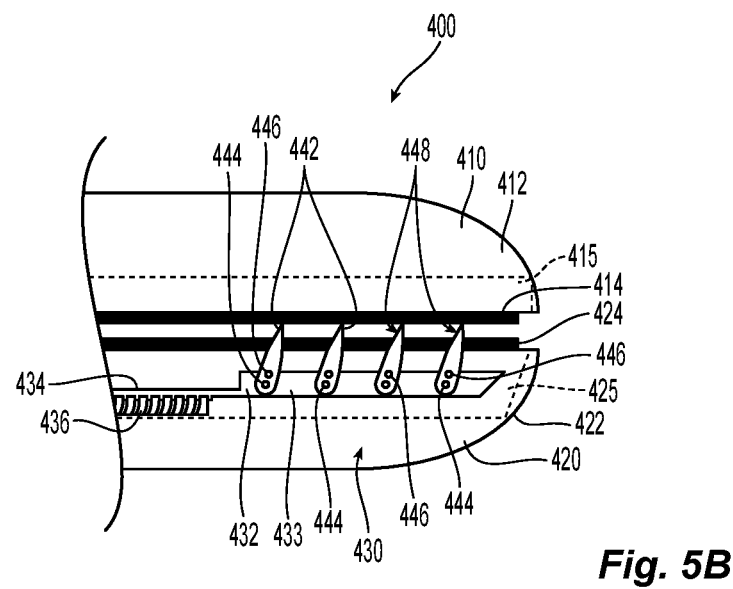
FIG. 5B is a longitudinal, transverse, cross-sectional view of the end effector assembly of FIG. 5A, wherein the knife chips thereof are disposed in an extended position.

With reference to FIGS. 5A and 5B, an end effector assembly provided in accordance with the present disclosure and configured for use with forceps 10 (FIGS. 1A-1B), forceps 210 (FIG. 2), robotic surgical system 1000 (FIG. 3A), and/or any other suitable surgical instrument or system is shown generally identified by reference numeral 400.

End effector assembly 400 is similar to end effector assembly 300 (FIGS. 4A-4C) and, thus, only differences therebetween will be described in detail below for purposes of brevity. End effector assembly 400 includes first and second jaw members 410, 420 each including a jaw housing 412, 422, a tissue-treating plate 414, 424, and a longitudinally-extending channel 415, 425, although in some embodiments only one jaw member 410, 420 includes a channel 415, 425, respectively.

One of the jaw members, e.g., jaw member 420, includes a cutting mechanism 430 housed within jaw housing 422 thereof. Cutting mechanism 430 includes an actuation shaft 432 slidably disposed within channel 426 of jaw member 432, a threaded drive screw 436 operably coupled to actuation shaft 432, and a plurality of spaced-apart knife chips 442 extending longitudinally within channel 425 and pivotably coupled to both jaw member 420 and actuation shaft 432. Actuation shaft 432 includes a body 433 and a proximal coupler 434 configured to operably couple actuation shaft 432 to threaded drive screw 436. More specifically, proximal coupler 434 may define threading disposed in meshed engagement with the threading on threaded drive screw 436 such that rotation of threaded drive screw 436 about a longitudinal axis thereof translates actuation shaft 432 through channel 425 and relative to jaw member 420. As an alternative to proximal coupler 434 engaging threaded drive screw 436, proximal coupler 434 may be configured to operably couple to any other suitable actuation mechanism e.g., a cable or pull-wire that is coupled to a motor or actuator, to effect translation of actuation shaft 432 through channel 425 and relative to jaw member 420. Regardless of the particular actuation mechanism utilized, the actuation mechanism is configured to extend through and/or around articulating components, pivoting components, and/or other components of the surgical instrument used with end effector assembly 400 so as not to be interrupted by or interrupt articulation, pivoting, etc. of the surgical instrument used with end effector assembly 400. The actuation mechanism may ultimately couple to a trigger, motor, or other suitable actuator for enabling selective actuation of cutting mechanism 430.

The plurality of spaced-apart knife chips 442 of knife assembly 430, as mentioned above, extends longitudinally within channel 425 and is pivotably coupled to both jaw member 420 and actuation shaft 432. More specifically, each knife chip 442 is pivotably coupled to actuation shaft 432 via a first pivot pin 444 and to jaw member 420 via a second pivot pin 446 (for example, on either side of channel 425). Each first pivot pin 444 is offset relative to the corresponding second pivot pin 446 of the respective knife chip 442. As a result of this configuration, translation of actuation shaft 432 through channel 425 and relative to jaw member 420 urges the knife chips 442 to pivot relative to jaw member 420 about the respective second pivot pins 446 thereof from a retracted position (FIG. 5A), wherein each knife chip 442 is disposed within channel 425 and does not extend therefrom, to an extended position (FIG. 5B), wherein each knife chip 442 extends from channel 425 towards jaw member 410 and, in some embodiments, at least partially into channel 415.

Each knife chip 442 defines at least one cutting surface 448 configured such that, upon pivoting of knife chips 442 from the retracted position to the extended position, the knife chips 442, led by cutting surfaces 448, are swept between jaw members 410, 420 to cut tissue grasped therebetween. Knife chips 442 may be arranged to define overlapping "sweep" patterns to ensure complete cutting of tissue grasped between jaw members 410, 420. Further, although four (4) knife chips 442 are illustrated in FIGS. 5A and 5B, greater or fewer knife chips 442 may alternatively be provided.

Figure 6A:
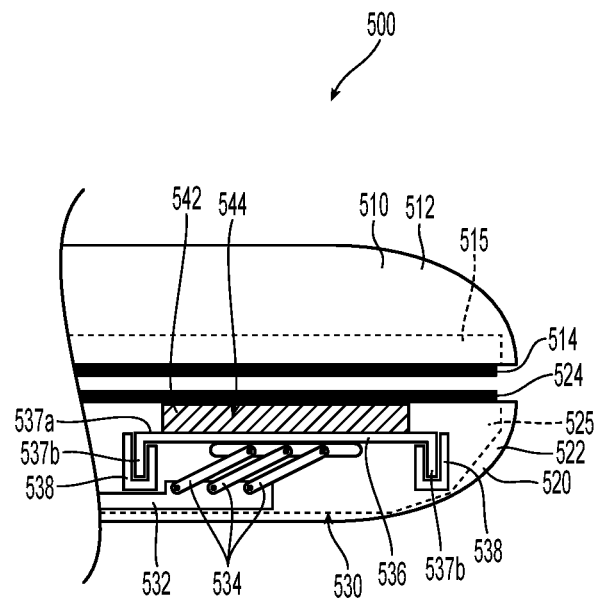
FIG. 6A is a longitudinal, cross-sectional view of another end effector assembly configured for use with the forceps of FIG. 1A, the forceps of FIG. 2, and/or the system of FIG. 3, wherein the knife thereof is disposed in a retracted position.
Figure 6B:
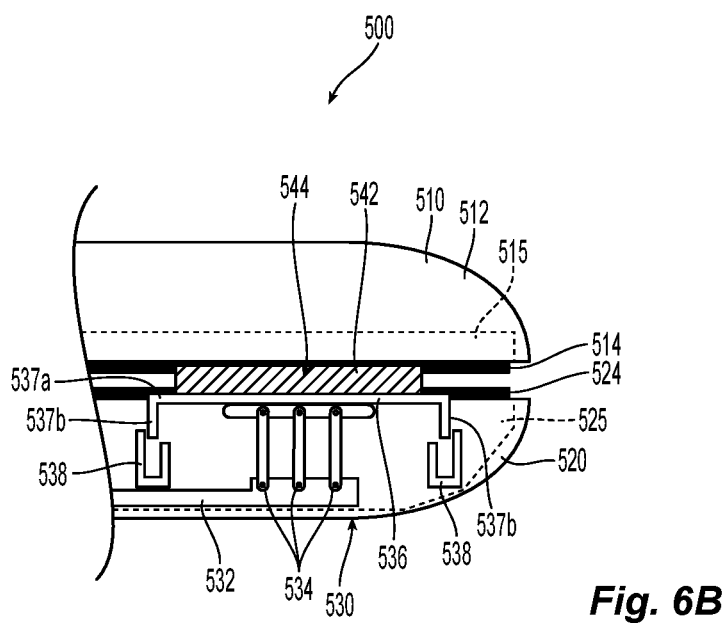
FIG. 6B is a longitudinal, transverse, cross-sectional view of the end effector assembly of FIG. 6A, wherein the knife thereof is disposed in an extended position.

With reference to FIGS. 6A-6B, an end effector assembly provided in accordance with the present disclosure and configured for use with forceps 10 (FIGS. 1A-1B), forceps 210 (FIG. 2), robotic surgical system 1000 (FIG. 3A), and/or any other suitable surgical instrument or system is shown generally identified by reference numeral 500.

End effector assembly 500 is similar to end effector assemblies 100, 100', 1100 (FIGS. 1A-1B, 2, 3A, respectively) and, thus, only differences therebetween will be described in detail below for purposes of brevity. End effector assembly 500 includes first and second jaw members 510, 520 each including a jaw housing 512, 522, a tissue-treating plate 514, 524, and a longitudinally-extending channel 515, 525, although in some embodiments, only one jaw member 510, 520 is provided with a channel 515, 525.

One of the jaw members, e.g., jaw member 520, includes a cutting mechanism 530 housed within jaw housing 522 thereof. Cutting mechanism 530 includes an actuation shaft 532, a plurality of linkages 534, a support base 536, a pair of guide brackets 538, and a knife 542. Actuation shaft 532 is configured to operably couple to an actuation mechanism including a threaded drive screw, cable, pull-wire, etc., to effect translation of actuation shaft 532 through channel 525 and relative to jaw member 520. Regardless of the particular actuation mechanism utilized, the actuation mechanism is configured to extend through and/or around articulating components, pivoting components, and/or other components of the surgical instrument used with end effector assembly 500 so as not to be interrupted by or interrupt articulation, pivoting, etc. of the surgical instrument used with end effector assembly 500. The actuation mechanism may ultimately couple to a trigger, motor, or other suitable actuator for enabling selective actuation of cutting mechanism 530.

Linkages 534 and pivotably coupled at the first ends thereof to actuation shaft 532 and at the second ends thereof to support base 536. Support base 536 includes a support surface 537a fixedly mounting knife 542 thereon, and a pair of guide legs 537b slidably received within guide brackets 538. Support base 536 and knife 542 are movably disposed within channel 525 of jaw member 520, while guide brackets 538 are fixedly engaged within jaw member 520. Knife 542 is initially disposed in a retracted position (FIG. 6A), corresponding to a proximal position of actuation shaft 532, wherein knife 542 is disposed within channel 525 and does not extend therefrom. Upon distal translation of actuation shaft 532 relative to and through jaw member 520, actuation shaft 532 urges linkages 534 to pivot, thereby urging support base 536 to move transversely within jaw member 520 towards jaw member 510. As a result of this movement of support base 536, knife 542 is urged to extend from channel 525, between jaw members 510, 520 and, in some embodiments, at least partially into channel 515 of jaw member 510 to an extended position (FIG. 6B). As can be appreciated via the above-detailed configuration, the advancement of knife 542 between jaw members 510, 520 cuts tissue grasped therebetween using the longitudinally-extending cutting edge 544 of knife 542.

Guide legs 537b of support base 536 and guide brackets 538 cooperate to generally confine movement of knife 542 to a transverse direction, e.g., towards and away from jaw member 510. However, in some embodiments, guide legs 537b and guide brackets 538 may be omitted to enable knife 542 to define a sweeping travel path including both transverse and longitudinal components of motion. In such embodiments, knife 542 may define one or more angled cutting surfaces to facilitate such "sweep" cutting.

Continuing with reference to FIGS. 6A and 6B, return of knife 542 to the retracted position may be effected by translating actuation shaft 532 back to its initial position, thereby pivoting linkages 534 back to their initial positions, or by translating actuation shaft 532 further in the actuation direction such that linkages 534 are pivoted beyond the peak positions thereof and back towards jaw member 520.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly configured for use with a surgical instrument or surgical system, the end effector assembly comprising:
    first and second jaw members each including an outer jaw housing and a tissue-treating plate, at least the second jaw member defining a longitudinally-extending channel and a longitudinally-extending guide track therethrough, at least one of the first or second jaw members pivotable relative to the other between a spaced-apart position and an approximated position; and
    a cutting mechanism disposed within the second jaw member, the cutting mechanism including:
        a knife disposed at least partially within the longitudinally-extending channel of the second jaw member, the knife defining a cutting surface and including a pivot pin, the pivot pin directly engaged with the longitudinally-extending guide track, the knife pivotable about the pivot pin relative to the second jaw member between a storage position, wherein the knife is fully disposed within the longitudinally-extending channel of the second jaw member and the cutting surface is oriented towards the first jaw member, and a use position, wherein the knife extends between the first and second jaw members and the cutting surface is oriented in a proximally-facing direction;
        a pull-wire extending through the second jaw member and coupled to the knife at a first location of the knife and proximate a distal end of the pull-wire, the pull-wire configured for proximal pulling relative to the second jaw member to initially pivot the knife from the storage position to the use position and to subsequently translate the knife through the longitudinally-extending channel of the second jaw member in a distal-to-proximal direction led by the cutting surface thereof; and
        a biasing member operatively coupled to the knife at a second location of the knife, the biasing member configured to remain operatively coupled to the knife throughout an entirety of longitudinal movement of the knife through the longitudinally-extending channel.

2. The end effector assembly according to claim 1, wherein the biasing member is operably coupled between the knife and the second jaw member, the biasing member configured to initially bias the knife distally relative to the longitudinally-extending channel of the second jaw member and to subsequently bias the knife towards the storage position.

3. The end effector assembly according to claim 1, wherein the longitudinally-extending guide track is configured to guide longitudinal translation of the pivot pin as the knife longitudinally translates through the longitudinally-extending channel.

4. The end effector assembly according to claim 3, wherein the longitudinally-extending channel is parallel to the longitudinally-extending guide track.

5. The end effector assembly according to claim 1, wherein the biasing member includes a spring.

6. The end effector assembly according to claim 1 wherein a first end of the biasing member is operatively coupled to a single portion of the knife.

* * * * *